(12) United States Patent
Nah et al.

(10) Patent No.: US 9,808,005 B2
(45) Date of Patent: Nov. 7, 2017

(54) ANTI-ALGAL BLOOM COMPOSITION CONTAINING WATER-SOLUBLE FREE AMINE CHITOSAN AS ACTIVE INGREDIENT, AND METHOD FOR REMOVING ALGAL-BLOOM USING SAME

(71) Applicant: SUNCHON INDUSTRY ACADEMIC COOPERATION FOUNDATION, Suncheon-si, Jeollanam-do (KR)

(72) Inventors: Jae-Woon Nah, Suncheon-si (KR); Mi-Kyeong Jang, Suncheon-si (KR); Seong-Cheol Park, Suncheon-si (KR)

(73) Assignee: SUNCHON INDUSTRY ACADEMIC COOPERATION FOUNDATION, Suncheon-si, Jeollanam-Do (KR)

(*) Notice: Subject to any disclaimer, the term of this patent is extended or adjusted under 35 U.S.C. 154(b) by 0 days.

(21) Appl. No.: 14/872,032

(22) Filed: Sep. 30, 2015

(65) Prior Publication Data

US 2016/0021880 A1   Jan. 28, 2016

Related U.S. Application Data

(63) Continuation of application No. PCT/KR2014/002600, filed on Mar. 27, 2014.

(30) Foreign Application Priority Data

Apr. 10, 2013  (KR) .................. 10-2013-0039379

(51) Int. Cl.
*A01N 43/16*  (2006.01)
*C08B 37/08*  (2006.01)

(52) U.S. Cl.
CPC ............ *A01N 43/16* (2013.01); *C08B 37/003* (2013.01)

(58) Field of Classification Search
None
See application file for complete search history.

(56) References Cited

U.S. PATENT DOCUMENTS

2009/0280984 A1   11/2009   Kao

FOREIGN PATENT DOCUMENTS

| JP | 07116642 A | 5/1995 | |
| JP | 2007246425 A | 9/2007 | |
| KR | 10-20030026191 A | 3/2003 | |
| KR | 10-20110023307 A | 3/2011 | |
| KR | WO 2011025133 A1 * | 3/2011 | ............ A01N 43/16 |
| WO | WO 2011/025133 A1 | 3/2011 | |

OTHER PUBLICATIONS

Pan et al., "Removal of cyanobacterial blooms in Taiju Lake using local soils. I. Equilibrium and kinetic screening on the flocculation of Microcystis aeruginosa using commercially available clays and minerals", Environ Pollution 141 206-212 (2006).*
WO2011025133—Nah—English.*
Chinese Office Action dated May 3, 2016 in connection with corresponding Chinese application serial No. 201480011416.1.
H. Zou, et al; Removal of cyanobacterial blooms in Taihu Lake using local soils . . . ; Environmental Pollution; vol. 141; 2006; pp. 201-205.
International Search Report dated Jul. 10, 2014 for Application No. PCT/KR2014/002600 with English translation.
Japanese Office Action dated Nov. 14, 2016, in connection with Japanese Patent Application No. 2016-507880.

* cited by examiner

*Primary Examiner* — Robert A Wax
*Assistant Examiner* — Thor Nielsen
(74) *Attorney, Agent, or Firm* — Lucas & Mercanti, LLP (57) ABSTRACT

The present invention relates to a composition for anti-green algae containing water-soluble free amine chitosan having the anti-algae activity against water-bloom forming algae as an active ingredient and a method for preparing the same. Particularly, the water-soluble free amine chitosan of the present invention can kill directly water-bloom forming algae, suggesting that it has excellent anti-green algae activity to inhibit water-bloom, and is non-toxic to freshwater organism cells. Therefore, the composition for anti-green algae containing the said water-soluble free amine chitosan as an active ingredient can be efficiently used as a safe anti-green algae composition applicable in the freshwater ecosystem including solidified dam, reservoir, lake, golf course water hazard, pond, freshwater fish farm, and fishing spot.

2 Claims, 7 Drawing Sheets

ANTI-ALGAL BLOOM COMPOSITION CONTAINING WATER-SOLUBLE FREE AMINE CHITOSAN AS ACTIVE INGREDIENT, AND METHOD FOR REMOVING ALGAL-BLOOM USING SAME

CROSS-REFERENCE TO RELATED APPLICATIONS

This application is a continuation of PCT/KR2014/002600, filed Mar. 27, 2014, which claims the benefit of Korean Patent Application No. 10-2013-0039379, filed Apr. 10, 2013, the contents of each of which are incorporated herein by reference.

BACKGROUND OF THE INVENTION

1. Field of the Invention

The present invention relates to a composition for anti-green algae containing water-soluble free amine chitosan having the anti-algae activity against water-bloom forming algae as an active ingredient and a method for removing green algae using the same.

2. Description of the Related Art

Water-bloom is a result of mass propagation and accumulation of floating algae (phytoplankton) in the water surface of eutrophicated lake or river where water flow is slow, which turns the water color into significant green. The environmental damage caused by such harmful water-bloom observed in between May and October reaches hundreds of billions of Korean Won, which is a significant environmental disaster. Water-bloom is easily developed when the top-water temperature is at least 23° C. for at least 3 consecutive days in the puddles or where the water flows very slowly like in solidified dam, reservoir, lake, golf course water hazard, pond, freshwater fish farm, and fishing spot, etc. Most of green algae found in Korea belong to blue-green algae and the identified algae species are at least 167 species of algae.

Once water-bloom is developed, algae grows in arithmetical progression, so that most of water oxygen is consumed by the algae, resulting in the eutrophication (oxygen deficiency) accompanying bad smell when it becomes worse. Fish in the water are suffering from oxygen deficiency and have difficulty in breathing because of algae attached on gill. Accordingly, the fishes float on the surface of water and cannot be adapted to a rapid change of water temperature, resulting in death. A mass propagation of blue-green algae is frequently observed recently in Nakdong River and Daecheong Reservoir in summer with water color change.

Once water-bloom is developed, the water system is limited in its use as drinking water or in industrial uses. So, it is not only a huge waste of costs but also a significant ecological problem causing other issues in other sectors such as society, economy, and environment as well. The overseas Korean companies are experiencing the direct or indirect damages from water-bloom, and the cases are increasing every year. The case of Azzurri, Argentina, is an example. Precisely, the company was sued for damages by water-bloom in the water treatment plant in Argentina that totaled 550 million dollars (Two of Korean companies which went to the area of Taihu Lake, China, were closed because of water-bloom as of July, 2007).

Another problem caused by the growth of water-bloom forming algae is the toxic cyclic peptide so called microcystin produced by them that might cause a disease in people who swim in the lake or pond where green algae proliferate or who drink water therefrom. The conventional algae control method which aiming at the destruction of algae eventually can rather accelerate the secretion of microcystin where water-bloom is densely developed. Mass secretion of microcystin is not just harmful to the growth of aquatic organisms but also harmful to human.

The water-bloom development is a significant environmental problem not just in freshwater but also in seaside. Water-bloom in the sea is developed by the sedimentation of abnormally proliferated Enteromorpha in shoreline. Water-bloom in the sea is reported from all parts of the world, for example the cases of Chesapeake Bay in USA, Bretagne in France, and Chentao in China are well known. In Japan, see water-bloom has been notified in Tokyo Bay, Seto Inland Sea, and many seaside areas of Kyushu since 1990. Water-bloom in the sea causes the deterioration of seaside landscape, bad smell by the decay of sea algae, and the extinction of fish and shellfish including Manila clam. So, Japanese local governments have been trying to remove and discard green algae with pouring hundreds of thousands of Japanese Yen every year. However, there is no efficient control method yet to remove green algae in the coast which grow every year.

A solution or countermeasure has been sought to minimize the damage by green algae. However, the conventional method or countermeasure established so far might cause problems in the $2^{nd}$ or $3^{rd}$ ecosystem and besides it takes a long time to be effective. Followings are the examples of the conventional methods to remove green algae.

First, one of the most conventional methods to remove green algae in freshwater is yellow loess (red clay) dispersal. Yellow loess is a mineral that has a high specific gravity, so that the electrical double-layers of the particle can be significantly condensed and precipitated easily, by which it can coagulate and precipitate green algae down to fresh water or sea water. This method is widely used in Korea to prevent and remove green algae. However, this method can cause secondary environmental pollution, so that it is not widely used in other countries. That is, when yellow loess is sprinkled where water is solidified or where the water flow is slow, micro yellow loess particles are precipitated with destroying other aquatic organisms. In addition, according to the recent report, even the precipitated algae can grow again after the dormant period, which might cause any secondary damage.

Next, a physical green algae control method is to dredge or replace the sedimentary layer to prevent green algae. When all the wastes and pollutants accumulated in the sedimentary layer either on land or fish farm are decomposed, they consumed dissolved oxygen and produce various toxic materials to cause water-bloom. So, as mentioned, this method is to dredge or replace the sedimentary layer. However, this method is not so effective in a big lake or huge dam where green algae are actually observed often.

Another method to control green algae is to build an artificial island or to install a shading net. This method, however, is not so effective in a wide area, either (non-patent reference 1). The deep aeration system that can supply oxygen is usable but only effective in shallow water in about 5 m in depth (non-patent reference 2). Besides, a recently developed device to destroy the membrane of harmful algae by using ultrasonic waves is now on the market (patent reference 1). However, this device also has a disadvantage that is other aquatic organisms might be affected by the strength of ultrasonic eaves. Such physical methods cost a lot to control green algae, suggesting that the usability is very limited.

Considering the above disadvantages of the conventional methods, the present inventors tried the pro-environmental non-toxic, not only to human but also to ecosystem, chitosan on water-bloom forming algae and as a result, the inventors confirmed that the treated chitosan demonstrated anti-algae effect on such water-bloom forming algae but had no toxicity to aquatic organisms, leading to the completion of the invention.

SUMMARY OF THE INVENTION

It is an object of the present invention to provide a composition for anti-green algae containing water-soluble free amine chitosan having the anti-algae activity against water-bloom forming algae as an active ingredient.

It is another object of the present invention to provide a method for removing green algae by sprinkling the composition for anti-green algae containing water-soluble free amine chitosan as an active ingredient in fresh water showing water-bloom.

In addition, it is also an object of the present invention to provide a use of the composition for anti-green algae containing the water-soluble free amine chitosan in the molecular weight of 20 kDa~100 kDa which demonstrates the anti-algae activity against water-bloom forming algae as an active ingredient.

To achieve the above objects, the present invention provides a composition for anti-green algae containing water-soluble free amine chitosan having the anti-algae activity against water-bloom forming algae as an active ingredient.

The present invention also provides a method for removing green algae by sprinkling the composition for anti-green algae containing water-soluble free amine chitosan as an active ingredient in fresh water showing water-bloom.

The water-soluble free amine chitosan of the present invention can kill directly water-bloom forming algae, suggesting that it has excellent anti-green algae activity to inhibit water-bloom, and is non-toxic to freshwater organism cells. Therefore, the composition for anti-green algae containing the said water-soluble free amine chitosan as an active ingredient can be efficiently used as a safe anti-green algae composition applicable in the freshwater ecosystem including solidified dam, reservoir, lake, golf course water hazard, pond, freshwater fish farm, and fishing spot.

BRIEF DESCRIPTION OF THE DRAWINGS

The application of the preferred embodiments of the present invention is best understood with reference to the accompanying drawings, wherein.

DETAILED DESCRIPTION OF THE INVENTION

Hereinafter, the present invention is described in detail.

The present invention provides a composition for anti-green algae containing the water-soluble free amine chitosan in the molecular weight of 20 kDa~100 kDa which demonstrates the anti-algae activity against water-bloom forming algae as an active ingredient.

The composition for anti-green algae of the present invention demonstrates the anti-algae activity against water-bloom forming algae, which are exemplified by *Microcystis aeruginosa, Scenedesmus obliquus,* and *Chlorella vulgaris.*

The water-soluble free amine chitosan included as an active ingredient in the composition for anti-green algae of the present invention can be prepared by the method comprising the following steps, but not always limited thereto:

inducing salt formation in the insoluble chitosan by using organic and inorganic acids, followed by enzyme decomposition to prepare chitosan polysaccharide (step 1);

treating organic acid or inorganic acid salt solution of the chitosan polysaccharide prepared in step 1) with trialkylamine (step 2)

adding an organic solvent to the mixed solution of step 2) to remove the organic or inorganic acid attached to the chitosan polysaccharide, resulting in the preparation of acid-free chitosan polysaccharide (step 3); and treating the acid-free chitosan polysaccharide solution prepared in step 3) with inorganic acid, followed by purification with activated carbon/ion exchange resin column to prepare the pure water-soluble free amine chitosan (step 4).

According to the method of the present invention, the prepared water-soluble free amine chitosan has high water-solubility and biological activity and has the molecular weight of 1 kDa~100 kDa.

The anti-algae composition of the present invention preferably contains the water-soluble free amine chitosan of 20 kDa~100 kDa having the anti-algae activity against water-bloom forming algae.

If the molecular weight of the water-soluble free amine chitosan of the present invention is less than 20 kDa, the chitosan still displays the anti-algae activity against water-bloom forming algae but the activity is too low to prevent or remove water-bloom. If the molecular weight of the chitosan is more than 100 kDa, it displays excellent anti-algae activity but displays toxicity against other aquatic organisms.

The anti-algae activity of the water-soluble free amine chitosan included in the composition for anti-green algae of the present invention as an active ingredient against water-bloom forming algae was evaluated. As a result, it was confirmed that the water-soluble free amine chitosan of the invention could inhibit the growth of *Microcystis aeruginosa*, *Scenedesmus obliquus*, and *Chlorella vulgaris* by 50% at the concentration of 0.024 g/L, suggesting that it can display excellent anti-algae activity against fresh water algae that cause water-bloom at a low concentration (see Experimental Example 1). Also, the water-soluble free amine chitosan of the present invention was confirmed not to have toxicity. Precisely, when the water-soluble free amine chitosan was treated to fresh water where carps live, it did not cause erythrocyte hemolysis in carp, suggesting that it did not have cytotoxicity (see Experimental Example 3). Further, in the experiment wherein the population of algae that cause water-bloom was increased, the water-soluble free amine chitosan displayed excellent water-bloom inhibition and elimination effect. When the water-soluble free amine chitosan of the invention was treated to the pond where water-bloom was actually growing, it displayed excellent anti-water-bloom activity therein (see Experimental Examples 4 and 5).

Therefore, since the water-soluble free amine chitosan in the molecular weight of 20 kDa~100 kDa of the invention has excellent anti-algae activity against water-bloom forming algae and at the same time does not cause cytotoxicity in fresh water organisms, suggesting that it has no harm on ecosystem, the composition for anti-green algae containing the said water-soluble free amine chitosan as an active ingredient can be efficiently used as a safe anti-green algae composition applicable in the freshwater ecosystem including solidified dam, reservoir, lake, golf course water hazard, pond, freshwater fish farm, and fishing spot.

The present invention also provides a method for removing green algae by sprinkling the composition for anti-green algae containing the water-soluble free amine chitosan in the molecular weight of 20 kDa~100 kDa which demonstrates the anti-algae activity against water-bloom forming algae as an active ingredient in fresh water showing water-bloom.

In addition, the present invention provides a use of the composition for anti-green algae containing the water-soluble free amine chitosan in the molecular weight of 20 kDa~100 kDa which demonstrates the anti-algae activity against water-bloom forming algae as an active ingredient.

Practical and presently preferred embodiments of the present invention are illustrative as shown in the following Examples.

However, it will be appreciated that those skilled in the art, on consideration of this disclosure, may make modifications and improvements within the spirit and scope of the present invention.

PREPARATIVE EXAMPLE 1

Preparation of Water-soluble Free Amine Chitosan 1

Step 1: Preparation of Chitosan Polysaccharide

5% chitosan solution was prepared by using lactic acid as a solvent. 5 units of chitosanase originated from *Bacillus pumilus* BN-262 was added to 100 mL of the said 5% chitosan solution (pH 5.0~5.5), followed by enzyme reaction at 40° C. for 36 hours. Upon completion of the reaction, the mixture was filtered by using a 1 μm pre-filter and then filtered again by using a hollow filter (molecular weight: 20 kDa). The obtained filtrate was concentrated by using the nanofilter system, followed by sterilization and drying with an air spray dryer. As a result, chitosan polysaccharide was obtained.

Step 2: Preparation of Acid-free Chitosan Polysaccharide

The obtained chitosan polysaccharide was dissolved in 1 L of PBS (pH 7.0), to which 0.52 L of triethylamine was slowly dropped. At this time, 1 equivalent of amine group of the chitosan oligosaccharide was reacted with 2 equivalents of triethylamine. The reaction mixture proceeded to reaction at room temperature for 2 hours, to which acetone was added, followed by stirring. Then, centrifugation was performed. The said procedure was repeated 2~3 times, followed by air drying and freeze-drying to obtain acid-free chitosan polysaccharide. At this time, centrifugation was performed at 4° C., 15,000 rpm, for 20 minutes by using Supra 30 K.

Step 3: Preparation of Water-Soluble Free Amine Chitosan 30 mL~50 mL of 0.001 N HCl was added to the chitosan polysaccharide prepared in step 2), followed by reaction for 2 hours. Acetone was added to the reaction mixture, which was stirred and centrifuged with the same conditions as described above. The said procedure was repeated 2~3 times, followed by air drying and freeze-drying. The dried product was dissolved in distilled water, and then purified by the activated carbon/ion exchange resin column. The obtained aqueous solution was freeze-dried. The product was then dissolved in water, followed by filtering with cellulose acetate membrane (permeation molecular weight: 20 kDa). As a result, the water-soluble free amine chitosan in the molecular weight of 20 kDa was obtained.

PREPARATIVE EXAMPLE 2

Preparation of Water-soluble Free Amine Chitosan 2

The water-soluble free amine chitosan in the molecular weight of 100 kDa was prepared by the same manner as described in Preparative Example 1 except that 100 kDa cellulose acetate membrane was used instead of kDa cellulose acetate membrane in step 3) of Preparative Example 1.

COMPARATIVE EXAMPLE 1

Preparation of Water-soluble Free Amine Chitosan 3

The water-soluble free amine chitosan in the molecular weight of 1 kDa was prepared by the same manner as described in Preparative Example 1 except that 1 kDa cellulose acetate membrane was used instead of 20 kDa cellulose acetate membrane in step 3) of Preparative Example 1.

COMPARATIVE EXAMPLE 2

Preparation of Water-soluble Free Amine Chitosan 4

The water-soluble free amine chitosan in the molecular weight of 3 kDa was prepared by the same manner as described in Preparative Example 1 except that kDa cellulose acetate membrane was used instead of 20 kDa cellulose acetate membrane in step 3) of Preparative Example 1.

COMPARATIVE EXAMPLE 3

Preparation of Water-soluble Free Amine Chitosan 5

The water-soluble free amine chitosan in the molecular weight of 5 kDa was prepared by the same manner as described in Preparative Example 1 except that kDa cellulose acetate membrane was used instead of 20 kDa cellulose acetate membrane in step 3) of Preparative Example 1.

COMPARATIVE EXAMPLE 4

Preparation of Water-soluble Free Amine Chitosan 6

The water-soluble free amine chitosan in the molecular weight of 10 kDa was prepared by the same manner as described in Preparative Example 1 except that 10 kDa cellulose acetate membrane was used instead of 20 kDa cellulose acetate membrane in step 3) of Preparative Example 1.

COMPARATIVE EXAMPLE 5

Preparation of Water-soluble Free Amine Chitosan 7

The water-soluble free amine chitosan in the molecular weight of 150 kDa was prepared by the same manner as described in Preparative Example 1 except that the enzyme reaction of step 1) and the filtration with 20 kDa cellulose acetate membrane of step 3) of Preparative Example 1 were not performed.

EXPERIMENTAL EXAMPLE 1

Evaluation of Anti-green Algae Activity of Water-soluble Free Amine Chitosan 1

To evaluate the anti-green algae activity of the water-soluble free amine chitosan of the present invention, the following experiment was performed.

*Microcystis aeruginosa*, *Scenedesmus obliquus*, and *Chlorella vulgaris* distributed from Korea Marine Microalgae Culture Center were used as the water-bloom forming algae for the evaluation of the anti-green algae activity. The algae were cultured in BG-11 media supplemented with $NaNO_3$ (15 mg), $K_2HPO_4$ (40 mg), $MgSO_4 \cdot 7H_2O$ (75 mg), $CaCl_2 \cdot 2H_2O$ (36 mg), citric acid (6 mg), ferric ammonium citrate (6 mg), EDTA (1 mg), $NaCO_3$ (20 mg), $H_3BO_3$ (2.86 mg), $MnCl_2 \cdot 4H_2O$ (1.81 mg), $ZnSO_4 \cdot 7H_2O$ (0.222 mg), $CuSO_4 \cdot 5H_2O$ (0.079 mg), and $Co(NO_3)_2 \cdot 6H_2O$ (0.0494 mg/1 L) at 22° C. at 3,000 Lux with 14 h/10 h of light and dark cycle. The pre-cultured algae cells were diluted at the density of $2 \times 10^5$ cells/mL or $5 \times 10^5$ cells/mL, which were then inoculated in a 24-well micro-titrate plate. Each of the water-soluble free amine chitosans prepared respectively in Preparative Example 1, Preparative Example 2, and Comparative Examples 1~5 was diluted by ½ each time starting from the concentration of 6.25 (mg/mL)/well, which was added to the plate inoculated with the said strain. For the non-treated control, BG-medium not containing the water-soluble free amine chitosan was added thereto. During the culture for 2 days with the above culture condition, the population of algae was counted with a hemocytometer every 6 hours in order to determine 50% of inhibitory concentration (referred as $IC_{50}$ hereinafter). The results are shown in Table 1.

TABLE 1

| | $IC_{50}$ (g/L) | | |
|---|---|---|---|
| | *Microcystis aeruginosa* | *Scenedesmus obliquus* | *Chlorella vulgaris* |
| Preparative Example 1 | 0.39 | 0.097 | 0.049 |
| Preparative Example 2 | <0.012 | <0.024 | <0.012 |
| Comparative Example 1 | 12.5 | 25 | 0.195 |
| Comparative Example 2 | 1.56 | 0.56 | 0.049 |
| Comparative Example 3 | 1.56 | 0.39 | 0.049 |
| Comparative Example 4 | 0.78 | 0.195 | 0.049 |
| Comparative Example 5 | <0.012 | <0.024 | <0.012 |

As shown in Table 1, the water-soluble free amine chitosan of 20 kDa~100 kDa in the molecular weight of the present invention displayed excellent anti-algae activity against water-bloom forming algae. More precisely, the water-soluble free amine chitosan of the invention in the molecular weight of 20 kDa~100 kDa displayed excellent anti-algae activity against water-bloom forming algae such as *Microcystis aeruginosa*, *Scenedesmus obliquus*, and *Chlorella vulgaris*, molecular weight dependently. That is, the anti-algae activity of the water-soluble free amine chitosan in the molecular weight of 100 kDa was demonstrated as $IC_{50}$ of 0.024 g/L or under, and the anti-algae activity against water-bloom forming algae of the water-soluble free amine chitosan in the molecular weight of 20 kDa, particularly against *Chlorella vulgaris*, was as excellent as $IC_{50}$ of 0.049 g/L. In the meantime, while the chitosan having the greater molecular weight than 100 kDa of Comparative Example 5 displayed excellent anti-algae activity, those water-soluble free amine chitosans having the smaller molecular weight than 20 kDa, prepared in Comparative Examples 1~4, displayed the anti-algae activity at least when the chitosan was treated double the concentration to those algae, except to *Chlorella vulgaris*, compared with those chitosans having the molecular weight of 20 kDa~100 kDa. Therefore, it was confirmed that the water-soluble free amine chitosan having the molecular weight of 20 kDa~100 kDa of the present invention had excellent anti-algae activity against water-bloom forming algae.

The water-soluble free amine chitosan in the molecular weight of 20 kDa~100 kDa of the present invention was confirmed to have excellent anti-algae activity against water-bloom forming algae, suggesting that it is effective in reducing water-bloom and inhibiting the proliferation of water-bloom forming algae, so that the composition for anti-green algae containing the water-soluble free amine chitosan as an active ingredient can be efficiently used as a safe anti-green algae composition applicable in the freshwater ecosystem including solidified dam, reservoir, lake, golf course water hazard, pond, freshwater fish farm, and fishing spot.

EXPERIMENTAL EXAMPLE 2

Evaluation of Anti-green Algae Activity of Water-soluble Free Amine Chitosan 2

To evaluate the anti-green algae activity of the water-soluble free amine chitosan of the present invention, the following experiment was performed.

The water-bloom forming algae used in Experimental Example 1 were cultured in BG-11 media supplemented with NaNO$_3$ (15 mg), K$_2$HPO$_4$ (40 mg), MgSO$_4$.7H$_2$O (75 mg), CaCl$_2$.2H$_2$O (36 mg), citric acid (6 mg), ferric ammonium citrate (6 mg), EDTA (1 mg), NaCO$_3$ (20 mg), H$_3$BO$_3$ (2.86 mg), MnCl$_2$.4H$_2$O (1.81 mg), ZnSO$_4$.7H$_2$O (0.222 mg), CuSO$_4$.5H$_2$O (0.079 mg), and Co(NO$_3$)$_2$.6H$_2$O (0.0494 mg/1 L). The cultured algae were inoculated in a 24-well micro-titrate plate at the density of 10$^5$ cells/mL, to which the water-soluble free amine chitosan prepared in Preparative Example 2 was added at the concentration of mg/mL per well, followed by culture at 22° C. for 2 hours. For the non-treated control, BG-11 medium not containing the water-soluble free amine chitosan was added thereto. Upon completion of the culture, the media were observed under optical and fluorescent microscopes for visualization. The results are shown in FIG. 1 and FIG. 2.

Figure 1:
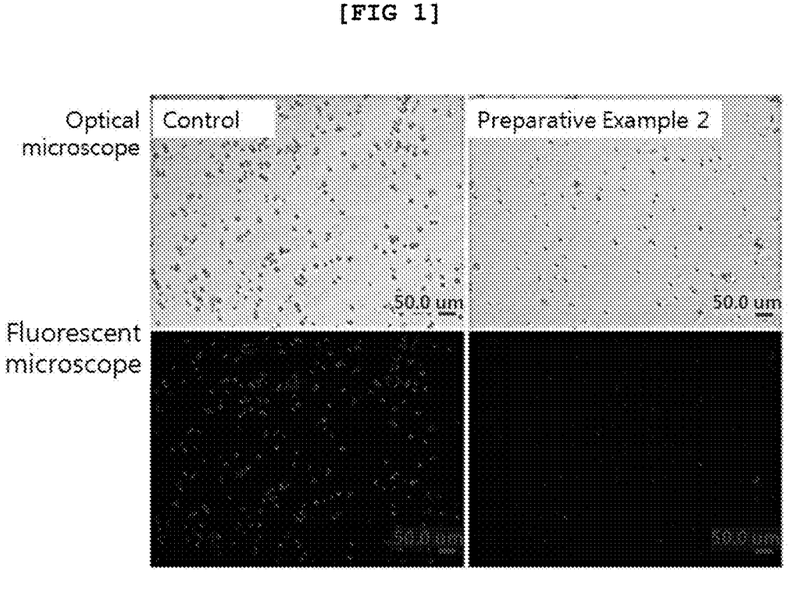
FIG. 1 is a photograph illustrating the anti-algae activity of the water-soluble free amine chitosan prepared in Preparative Example 2 against *Microcystis aeruginosa* which was observed under optical and fluorescent microscopes.
Figure 2:
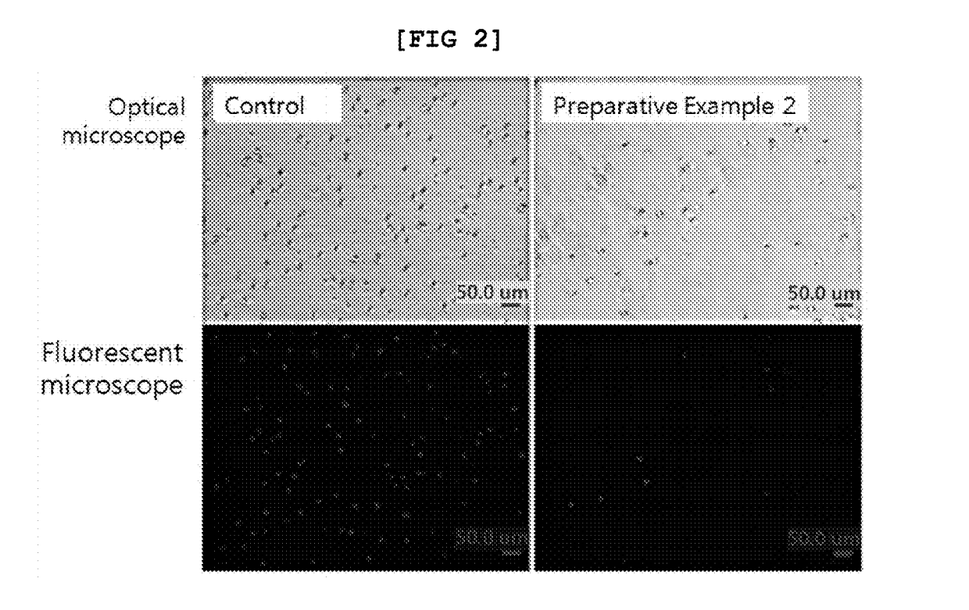
FIG. 2 is a photograph illustrating the anti-algae activity of the water-soluble free amine chitosan prepared in Preparative Example 2 against *Scenedesmus obliquus* which was observed under optical and fluorescent microscopes.

As shown in FIG. 1 and FIG. 2, the water-soluble free amine chitosan of the present invention demonstrated the anti-algae activity against water-bloom forming algae. Green algae emit fluorescence themselves when they are alive but cannot emit fluorescence when they are dead. The observation under fluorescent microscope was performed based on that fact. From the observation of the non-treated control group, it was confirmed that the number of the organisms was maintained and the morphology thereof was not changed. However, when the algae were treated with the water-soluble free amine chitosan prepared in Preparative Example 2, the number of the algae was significantly reduced, compare with the non-treated control group, and the increase of the population was not observed at all. Therefore, it was confirmed that the water-soluble free amine chitosan of the present invention can cause the death of water-bloom forming algae.

The water-soluble free amine chitosan in the molecular weight of 20 kDa~100 kDa of the present invention was confirmed to have excellent anti-algae activity against water-bloom forming algae, suggesting that it is effective in reducing water-bloom and inhibiting the proliferation of water-bloom forming algae, so that the composition for anti-green algae containing the water-soluble free amine chitosan as an active ingredient can be efficiently used as a safe anti-green algae composition applicable in the freshwater ecosystem including solidified dam, reservoir, lake, golf course water hazard, pond, freshwater fish farm, and fishing spot.

Experimental Example 3

Evaluation of Cytotoxicity to Freshwater Organisms

To evaluate cytotoxicity of the water-soluble free amine chitosan in the molecular weight of 20 kDa~100 kDa of the present invention to the freshwater organisms, the following experiment was performed.

First, blood was taken from the fresh water carp. The blood was treated with heparin to prevent coagulation and then erythrocytes were separated. The density of the separated erythrocytes was regulated to be 8%, which were treated with the water-soluble free amine chitosans respectively prepared in Preparative Examples 1 and 2 and Comparative Examples 1~5 diluted two fold every time from the concentration of 10 mg/mL. Two hours later, the supernatant was separated and the free hemoglobin was measured by microplate reader to calculate erythrocyte hemolysis. The results are shown in FIG. 3.

Figure 3:
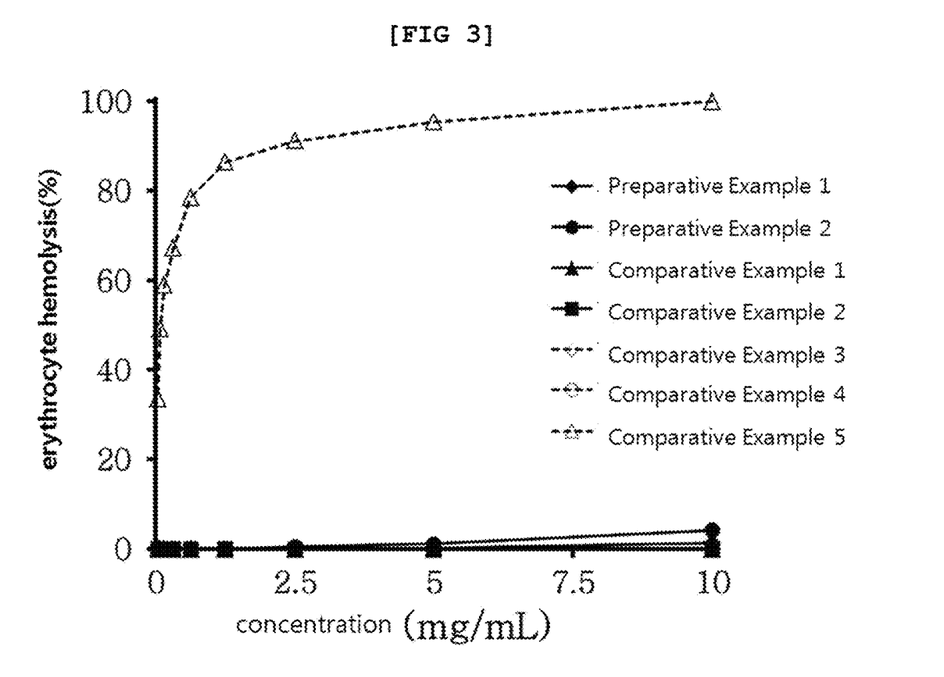
FIG. 3 is a graph illustrating the effect of the water-soluble free amine chitosans prepared in Preparative Example 1, Preparative Example 2, and Comparative Examples 1~4 on the erythrocyte hemolysis of carp that is one of limnobios.

As shown in FIG. 3, the water-soluble free amine chitosan in the molecular weight of 20 kDa~100 kDa of the present invention was confirmed not to have cytotoxicity to the freshwater organisms. More precisely, the water-soluble free amine chitosans prepared in Preparative Examples 1 and 2 showed as low hemolysis rate as less than 5% regardless of the concentration. In the meantime, the water-soluble free amine chitosan having the greater molecular weight than 100 kDa prepared in Comparative Example 5 displayed a high hemolysis rate even at a low concentration. Therefore, it was confirmed that the water-soluble free amine chitosan of the present invention was safe without cytotoxicity to the freshwater organisms.

The water-soluble free amine chitosan in the molecular weight of 20 kDa~100 kDa of the present invention was confirmed not only to have excellent anti-algae activity against water-bloom forming algae but also to be safe in the freshwater organisms without causing cytotoxicity therein, indicating that it does not cause any secondary problem in ecosystem, so that the composition for anti-green algae containing the water-soluble free amine chitosan as an active ingredient can be efficiently used as a safe anti-green algae composition applicable in the freshwater ecosystem including solidified dam, reservoir, lake, golf course water hazard, pond, freshwater fish farm, and fishing spot.

EXPERIMENTAL EXAMPLE 4

Evaluation of Green Algae Removing Effect of Water-soluble Free Amine Chitosan 1

To evaluate the green algae removing effect of the water-soluble free amine chitosan of the present invention, the following experiment was performed.

*Microcystis aeruginosa* and *Scenedesmus obliquus* pre-cultured under the same culture condition as described in Experimental Example 1 were loaded in T flask at the density of at least 10$^6$ cells, which were treated with 24 mg/L of the water-soluble free amine chitosan prepared in Preparative Example 2. The number of water-bloom forming algae was counted by using a hemocytometer every 6 hours, and 24 hours later the turbidity of water was observed. At this time, the medium not containing the water-soluble free amine chitosan was used as the non-treated control. The results are shown in FIG. 4 and FIG. 5.

Figure 4:
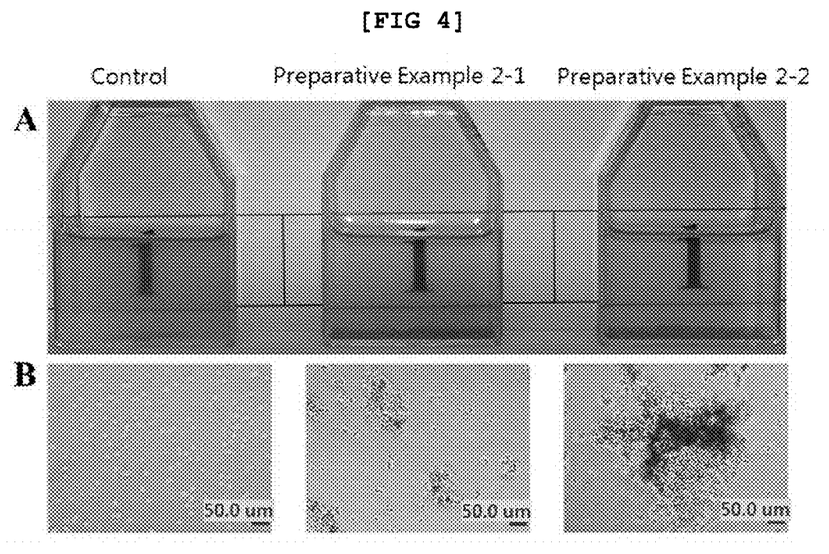
FIG. 4 is a photograph illustrating the anti-algae activity of the water-soluble free amine chitosan prepared in Preparative Example 2 against *Microcystis aeruginosa*, observed 4 and 36 hours after the treatment of the water-soluble free amine chitosan to the culture medium thereof (Preparative Example 2-1 presents the culture medium 4 hours after the treatment of the water-soluble free amine chitosan; and Preparative Example 2-2 presents the culture medium 36 hours after the treatment of the water-soluble free amine chitosan).
Figure 5:
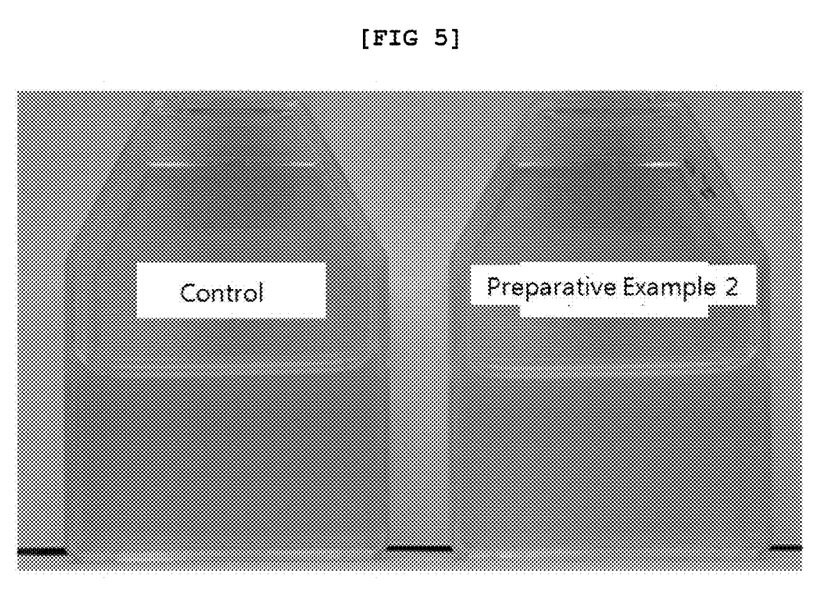
FIG. 5 is a photograph illustrating the anti-algae activity of the water-soluble free amine chitosan prepared in Preparative Example 2 against *Scenedesmus obliquus*, observed 36 hours after the treatment of the water-soluble free amine chitosan to the culture medium thereof.

As shown in FIG. 4 and FIG. 5, the water-soluble free amine chitosan of the present invention was confirmed to have the anti-algae activity against water-bloom forming algae such as *Microcystis aeruginosa* and *Scenedesmus obliquus*. More precisely, the non-treated group that was not treated with the water-soluble free amine chitosan showed a high turbidity in water like suspension, wherein the number of algae that cause water-bloom such as *Microcystis aeruginosa* and *Scenedesmus obliquus* were increased. In the meantime, when treated with the water-soluble free amine chitosan of the invention, the turbidity of water was decreased and water became clearer, wherein the dead algae were precipitated on the bottom of the flask. Therefore, it was confirmed that the water-soluble free amine chitosan of the present invention had the anti-algae activity against those algae that cause water-bloom.

The water-soluble free amine chitosan in the molecular weight of 20 kDa~100 kDa of the present invention was confirmed to have excellent anti-algae activity against water-bloom forming algae, suggesting that it is effective in reducing water-bloom and inhibiting the proliferation of water-bloom forming algae, so that the composition for anti-green algae containing the water-soluble free amine chitosan as an active ingredient can be efficiently used as a safe anti-green algae composition applicable in the freshwater ecosystem including solidified dam, reservoir, lake, golf course water hazard, pond, freshwater fish farm, and fishing spot.

EXPERIMENTAL EXAMPLE 5

Evaluation of Green Algae Removing Effect of Water-soluble Free Amine Chitosan 2

To evaluate the green algae removing effect of the water-soluble free amine chitosan of the present invention in the fresh water where the water-bloom has actually been developed, the following experiment was performed.

First, 700 L of water taken from a pond where water-bloom has been significant was transferred into a water-bath. Then, 60 mg/mL of the water-soluble free amine chitosan prepared in Preparative Example 2 of the present invention was treated thereto. 1 hour~12 hours later, water in the water bath was observed and photographed. The results are shown in FIG. 6 and FIG. 7.

Figure 6:
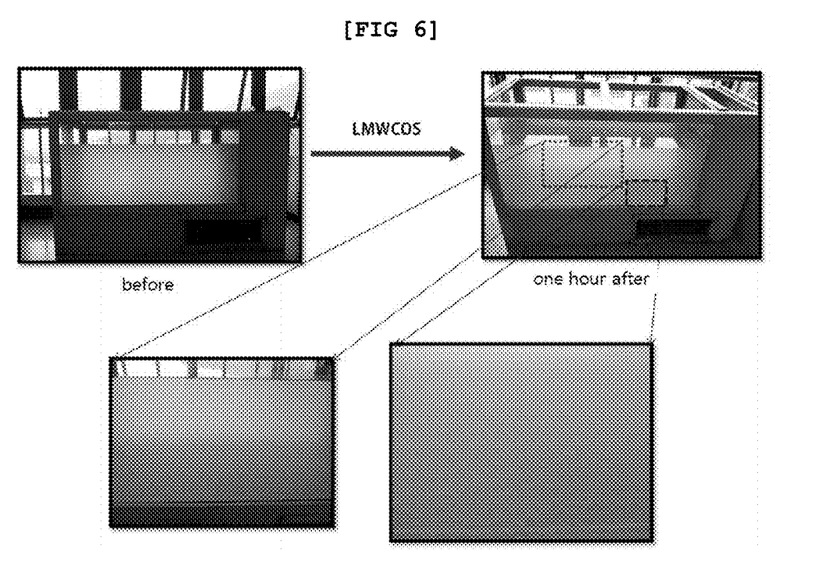
FIG. 6 is a photograph illustrating the changes of the pond showing water-bloom observed one hour after the treatment of the water-soluble free amine chitosan prepared in Preparative Example 2.
Figure 7:
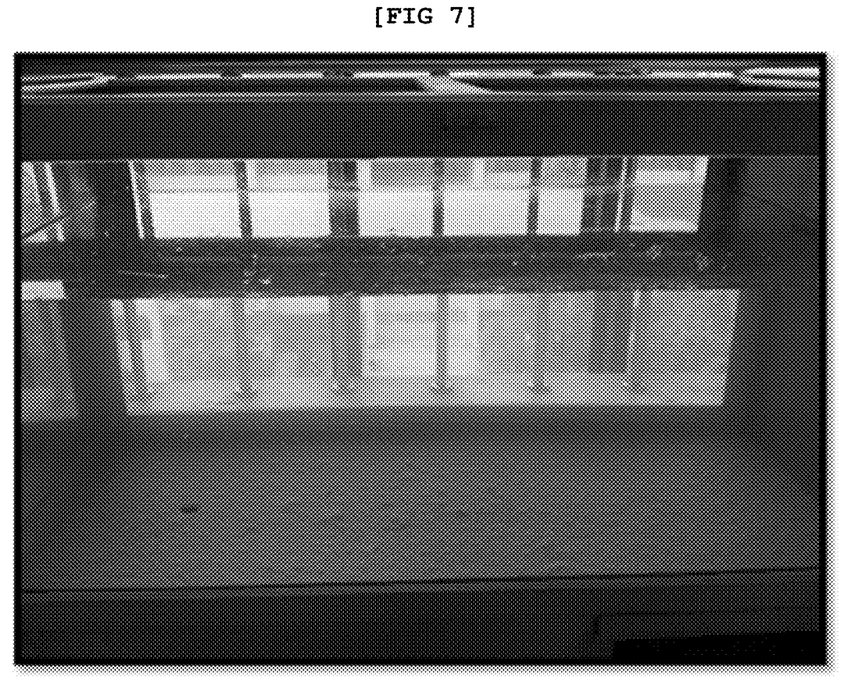
FIG. 7 is a photograph illustrating the changes of the pond showing water-bloom observed 12 hours after the treatment of the water-soluble free amine chitosan prepared in Preparative Example 2.

As shown in FIG. 6 and FIG. 7, the water-soluble free amine chitosan of the present invention demonstrated excellent anti-algae activity against those algae that cause water-bloom which had actually been in the course of proliferation in the pond. More precisely, as shown in FIG. 6, when the pond water was treated with the water-soluble free amine chitosan prepared in Preparative Example 2, those algae that cause water-bloom in the pond were dead and precipitated one hour after the treatment. As shown in FIG. 7, 12 hours after the pond water was treated with the water-soluble free amine chitosan, all the algae that had been causing water-bloom were dead and precipitated, and as a result the water became clearer with confirming the turbidity was lower. Therefore, it was confirmed that the water-soluble free amine chitosan of the present invention was excellent in removing green algae in the fresh water where water-bloom was developed.

The water-soluble free amine chitosan in the molecular weight of 20 kDa~100 kDa of the present invention was confirmed to have excellent anti-algae activity against water-bloom forming algae, suggesting that it is effective in reducing water-bloom and in inhibiting the proliferation of water-bloom forming algae, and also is excellent in removing green algae in the fresh water where water-bloom is actually developed, so that the composition for anti-green algae containing the water-soluble free amine chitosan as an active ingredient can be efficiently used as a safe anti-green algae composition applicable in the freshwater ecosystem including solidified dam, reservoir, lake, golf course water hazard, pond, freshwater fish farm, and fishing spot.

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended Claims.

We claim:

1. A method for removing algae in a fresh water ecosystem comprising the step of
sprinkling onto a freshwater ecosystem exhibiting a water algae bloom a composition consisting essentially of a water-soluble free amine chitosan having a molecular weight range of 20 kDa~100 kDa, wherein the composition demonstrates an anti-algal activity against water-bloom forming algae.

2. The method of claim 1, wherein the method for removing algae is performed to one or more water-bloom forming algae selected from the group consisting of *Microcystis aeruginosa*, *Scenedesmus obliquus*, and *Chlorella vulgaris*.

* * * * *